United States Patent [19]

Bach et al.

[11] 4,389,879

[45] Jun. 28, 1983

[54] METHOD AND APPARATUS FOR DETERMINING THE COLLOID INDEX IN LIQUIDS

[76] Inventors: Dieter Bach, Lilienweg 43, D-7014 Kornwestheim; Heiner G. Jäckle, Rotenwaldstrasse 179, D-7000 Stuttgart; Kurt Marquardt, Eschelbacher Weg 33, D-7031 Holzgerlingen, all of Fed. Rep. of Germany

[21] Appl. No.: 241,035

[22] Filed: Mar. 6, 1981

[30] Foreign Application Priority Data

Mar. 10, 1980 [DE] Fed. Rep. of Germany ....... 3009130

[51] Int. Cl.³ ........................................... G01N 15/00
[52] U.S. Cl. ..................................... 73/61 R; 73/61.2
[58] Field of Search ......................... 73/61 R, 61.2, 53

[56] References Cited

U.S. PATENT DOCUMENTS

| | | | |
|---|---|---|---|
| 3,271,999 | 9/1966 | Dwyer et al. | 73/61 R |
| 3,308,649 | 3/1967 | Colechia | 73/61 R |
| 3,371,786 | 3/1968 | Fann | 73/61 R X |
| 3,746,167 | 7/1973 | Arthur | 73/61 R X |
| 4,020,676 | 5/1977 | Nuxhall et al. | 73/61 R |

FOREIGN PATENT DOCUMENTS 1161792 8/1969 United Kingdom ............... 73/61 R

*Primary Examiner*—E. R. Kazenske
*Assistant Examiner*—Joseph W. Roskos
*Attorney, Agent, or Firm*—Fleit, Jacobson & Cohn

[57] ABSTRACT

In a system for determining the colloid index in a liquid, an amount of the liquid is taken from the body of liquid and passed through a measuring filter under pressure. The respective volumes of liquid which are passed through the measuring filter and the respective periods of time for that purpose are correlated, in a plurality of successive steps, and the change in the respective amounts of liquid or periods of time is used as a measurement for determining the colloid index, or the change in the amount of liquid flowing through the filter with respect to time is continuously detected.

9 Claims, 2 Drawing Figures

METHOD AND APPARATUS FOR DETERMINING THE COLLOID INDEX IN LIQUIDS

BACKGROUND OF THE INVENTION

It is often important or desirable to determine the colloid index (often referred to alternatively as the silting index or fouling index) in a liquid such as water, for example in the treatment of water. Such a method, and a suitable apparatus for carrying out the method, may be used for example for the following operations:

monitoring the degree of efficiency of the precleaning stage of a reverse osmosis installation;

monitoring reverse osmosis installations;

monitoring the quality of high-purity water after a very fine filtering stage;

monitoring filtering installations, for example sand or multi-layer filters, in water treatment, instead of measuring the degree of clouding;

monitoring boiler feed water and condensate; and monitoring very pure water in regard to contamination due to microorganisms.

At the present time, increasing importance is being attributed to water cleaning and purification installations which operate on the principle of reverse osmosis, in the desalification of water. In such an arrangement, the water to be desalified is pressed under high pressure through membranes which are of such a nature that the molecules of water and substances contained in the water are separated. When that is done however, there is the danger that the membranes may become blocked due to particular kinds of substances in the water. This blockage effect results in losses in respect of permeability, which are irreversible, and that can cause the reverse osmosis membranes to become completely useless. Such a breakdown not only causes an interruption in operation of the equipment, but also increases the operating cost thereof as the membranes are relatively expensive items.

SUMMARY OF THE INVENTION

An object of the present invention is to provide a method and apparatus for determining the colloid index of a liquid in a quick and easy manner.

A further object of the invention is to provide a method and apparatus which permit monitoring of a liquid to be treated, for ascertaining the colloid index thereof.

A still further object of the present invention is to provide a method and apparatus for use in a liquid treatment process such as water desalification, for continuously monitoring the liquid in respect of the presence of substances which are liable to cause blockage of a membrane.

A method of determining the colloid component or index of a liquid such as water provides that an amount of the liquid, referred to herein as the measuring liquid, is taken from the liquid in a branch conduit, during or after or within steps involved in the treatment of the liquid, and passed through a measuring filter under an applied pressure. The change in the amount of measuring liquid which can flow through the filter, with respect to time, is determined and used as a measurement for determining the colloid index. In one form of the method, the respective volumes of measuring liquid which are passed through the measuring filter within respective predetermined periods are determined in a plurality of successive steps, or alternatively, the periods of time required for respective predetermined volumes of liquid to pass through the filter are determined in successive steps. In another form of the method, the change in the measuring liquid flowing through the measuring filter, with respect to time, is continuously determined.

The liquid which is filtered through the measuring filter may be collected, and the operation of measuring the volume of liquid and the automatic control action in respect of building up from time to time a reserve store of filtered liquid may be effected by means of a vertically adjustable level sensing device.

An apparatus for determining the colloid index in a liquid such as water, for example in processing or treating water, comprises a pressure means including a pressure chamber which can be fitted to a measuring membrane for pressing liquid through a measuring filter. A collecting and measuring container is arranged below the measuring filter, for the liquid pressed therethrough, and volume and time measuring means are provided for timing various phases of operation of the apparatus, and for measuring the respective volumes of liquid. The apparatus includes a time control circuit which controls the opening of an inlet valve through which measuring liquid flows into the pressure chamber by way of a pressure control means, and the closing of an outlet valve arranged at the outlet of the collecting and measuring container. After the expiry of a given period of time, theoutlet valve is opened again, and remains opened for a given test period. After expiry of the test period, the outlet valve is closed for a given period of time, after which the inlet valve is also closed.

The above-mentioned time control circuit operates in dependence on the height setting of an adjustable-height level switch which produces an electrical signal when the level of liquid in the container reaches the level of the level switch.

The container has a filling pipe which extends into the vicinity of the liquid outlet at the bottom of the container. The measuring liquid which is pressed through the measuring filter is introduced into the container, through the filling pipe.

The height of the pressure chamber forming part of the pressure means may be greater than the diameter of any air bubbles which may occur in the liquid in the pressure chamber, while the container may be of varying diameters, arranged in a step configuration.

A support screen or filter means may be disposed in a closure member which covers the container, the screen supporting the measuring filter. The closure member may have a funnel-shaped or hopper-shaped opening below the screen, which opens at its lower, reduced-dimension end into the filling pipe which is secured at its upper end in the closure member. The measuring filter may be in the form of a membrane filter strip or band which is passed through the pressure chamber in a stepwise manner from a supply roller on to a take-up roller.

In the system of the invention therefore, liquid may be taken from the main body of liquid in a by-pass conduit during or after or within steps forming part of the process of treating the liquid. The change in the amount of liquid which flows through the measuring filter, with respect to time, is used as a measurement for determining the colloid content or index of the liquid. The values which are determined in discontinuous measuring methods of this kind are referred to as the silting index, fouling index or colloid index.

One system of this nature provides for determining the periods of time taken by respective volumes of the liquid to pass through the measuring filter, during a plurality of successive method steps. Alternatively, the system may provide for determining the volumes which pass through the measuring filter within predetermined periods of time. The change in through-flow of liquid may also be determined continuously.

In accordance with the invention therefore, manual measuring operations, which were hitherto highly time-consuming, for determining the desired measuring parameters, can advantageously be performed by means of an automatic, continuous or quasi-continuous measuring operation.

An apparatus for carrying out a method as set forth hereinbefore has a collecting and measuring container for collecting the liquid such as water which is pressed through the measuring filter. That liquid is passed into the container by means of a pipe which extends into the vicinity of the bottom of the container, thus resulting in the surface of the liquid in the container being undisturbed and thus also providing for precise determination of the amount of liquid in the container. It is also possible for the liquid which is pressed through the filter during the test period to be taken to the direct vicinity of the outlet of the container, at the bottom thereof.

The pressure chamber which is directly above the measuring filter and which contains the pressurized measuring liquid when it is being pressed through the filter may advantageously be of such a dimension that any air bubbles which may occur in the pressure chamber can escape upwardly so that the surface of the filter is free of bubbles. The height of the pressure chamber is therefore greater than the maximum possible diameter of air bubbles. The pressure chamber is advantageously about 10 mm in height.

It is advantageously possible to provide for monitoring of the manner of performance of a treatment process, for example a process for purifying the liquid, more particularly before it passes into a membrane desalisification unit; for example, it is possible to ascertain the result of the treatment effected in any individual stages of the process. Parts of the treatment installation may also be protected by virtue of the ability to determine the proportion of harmful substances in the liquid therein. Particularly in the treatment of water, it is constantly possible to obtain information about the likelihood of irreversible blockage of the membrane used in the treatment process. This therefore provides both active protection for the parts of the equipment which are used in the treatment process, for example reverse osmosis membranes, and also a possible way of controlling the process in any preliminary, intermediate or final purification stages as may be required.

DESCRIPTION OF THE PREFERRED EMBODIMENT

Figure 1:
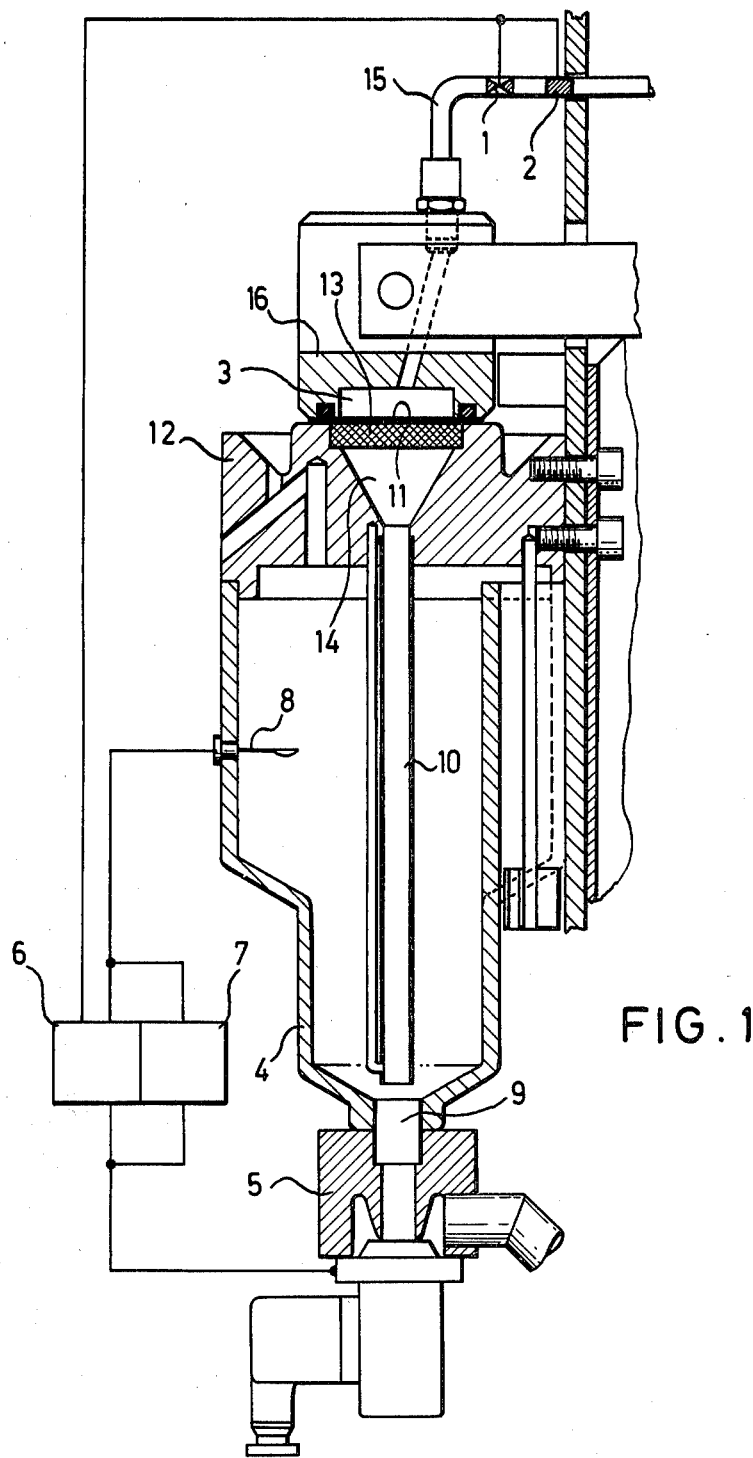
FIG. 1 shows a view in vertical section of a measuring apparatus.

A method and apparatus according to the principles of this invention will now be described. Reference is first made to FIG. 1 showing a measuring apparatus which includes a collecting and measuring container or vessel 4. The container 4 is covered and closed at its upper end by means of a closure member or cover 12 which carries a supporting screen member 13 on which a measuring filter 11 is mounted. Formed in the cover 12, below the screen member 13, is an opening 14 which is of a generally funnel-like configuration and whose downwardly pointing end opens into a filling pipe 10 which in turn is fixed in the cover 12.

The filling pipe 10 extends lengthwise of the measuring container 4, that is to say, vertically in the illustrated position, into the vicinity of the bottom or outlet end thereof, as indicated at 9. An outlet valve 5 is provided at the outlet 9.

The apparatus further comprises an inlet valve 1 which provides for control in respect of the intake of measuring liquid into a pressure chamber 3 through a feed conduit 15, and a pressure control means 2 for controlling the pressure of liquid supplied to the chamber. The measuring liquid is taken from a body of liquid which for example may be the subject of a treatment process such as purification or desalification.

The pressure chamber 3 as referred to above is provided in a clamping head member 16 which can be fitted to the cover 12 in such a way as to be liquid-tightly sealed around the measuring filter 11. The inlet valve 1 and the outlet valve 5 are controlled by means of a time control circuit 6 which operates in dependence on a vertically adjustable level detector or switching means 8. The switch 8 is thus arranged to respond when it detects a given level and thus a given volume of liquid in the container 4.

The apparatus further comprises a time measuring circuit 7 which is also connected to the level switch 8, for time measurement operations. The circuit 7 is thus operable to measure the period of time which is required for the container 4 to be filled with a given volume of liquid, that volume being preset by the positioning of the switch 8. Preferably, the container 4 is of a stepped configuration as shown, that is to say, it has a plurality of portions of different diameters, so that even small volumes of liquid can be determined, by reference to the height to which the container 4 is filled with liquid, with a sufficient degree of accuracy.

Figure 2:
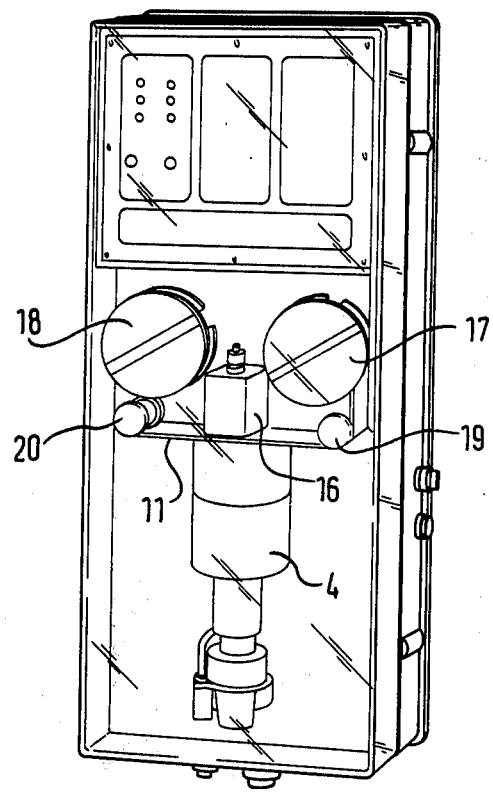
FIG. 2 shows a perspective view of an arrangement for mounting and guiding the measuring filter.

Reference is now made also to FIG. 2 which shows that the measuring filter 11 may be in the form of a membrane filter strip or band which is passed from a supply or storage reel 18 around a direction-changing roller 20 and through the pressure chamber defined by the member 16. The member 16 bears against and grips the measuring filter strip 11 and thus seals against it, thereby forming a defined filter surface area on the filter strip, in the pressure chamber 3. The apparatus also has a drive means (not shown), for example an electric motor, for clamping the member 16 to the filter strip and for lifting it therefrom. The filter strip 11, upon leaving the pressure chamber, is passed around a direction-changing roller 19 and wound on to a take-up reel 17.

The illustrated apparatus may be used for example for performing the following method:

During a first step of the method, the measuring liquid which is taken from the main body of the liquid which has been, is being or will be subjected to processing, is passed under the control of the inlet valve 1 through the conduit 15 into the pressure chamber 3 and pressed through the filter 11 under a pressure for example of 2 bars as set by the means 2. The outlet valve 5 remains closed at this time. The period of time $t_1$ required for the container 4 to be filled up to the position of the level switch 8 is measured by the circuit 7. The volume of liquid which can be preset by the positioning of the level switch 8 may typically be set for example at 100 or 500 ml.

The outlet valve 5 is then opened under the control of the circuits 6 and 7, to empty the container 4. With the outlet valve 5 still in an open condition, measuring liquid is pressed through the measuring filter 11 for a given period (test time T), again with a pressure for example of 2 bars being applied to the measuring liquid passing through the filter. In this operation, any filterable substance which may be contained in the liquid passing through the filter are retained thereby. The measuring liquid corresponds to the liquid which is supplied to reverse osmosis membranes for example in a liquid treatment cycle, such as in the desalification of water.

At the end of the test period T, which may be for example 5 or 15 minutes, the outlet valve 5 is closed by circuit 7 and the period of time required for the measuring liquid to re-fill the container 4 to the level of the switch 8 is again measured. This period of time is referred to as the second filling time $t_2$. The colloid component or index (CI) is determined in accordance with the formula set out below, and an evaluation circuit means (not shown) may be provided for determining the colloid index:

$$CI = \frac{\left(1 - \frac{t_1}{t_2}\right) \cdot 100}{T}$$

This formula is also disclosed for defining the blockage index in 'Technical Bulletin' No 491 of Mar. 1, 1976, issued by DuPont.

This system thus makes it possible continuously and accurately to obtain information about the colloid index during the treatment of a liquid.

In a modified form of the method of the invention, instead of determining the respective periods of time taken to fill the container 4 to the level preset by the level detector 8, it is possible to determine the volume of measuring liquid which is pressed through the measuring filter in given periods of time, possibly on a continuous basis.

Various modifications may be made in the above-described method and apparatus, without thereby departing from the scope and spirit of the invention.

We claim:

1. Apparatus for determining the colloid index of a liquid, comprising: conduit means for supplying measuring liquid from a body of liquid for the purposes of performing a colloid measuring operation on said measuring liquid; a measuring filter for filtering the measuring liquid supplied by the conduit means; below the measuring filter, a collecting and measuring container for collecting liquid which is passed through the filter; above the measuring filter a pressure means including a pressure chamber for pressing measuring liquid through the filter; an inlet valve on said conduit means for controlling the flow of measuring liquid into the pressure chamber; an outlet valve at the outlet of the container, for controlling the discharge of measuring liquid therefrom; means for measuring the volume of liquid in the container; and a time control means operable to control the opening and closing of the inlet and outlet valves and adapted to open the inlet valve and close the outlet valve to cause measuring liquid to flow through the measuring filter and be collected in said container, and adapted to open the outlet valve after measuring liquid has passed into said container for a given period of time and to hold the outlet valve open for a test period, and the time control means being further adapted to close the outlet valve for a given period of time after expiry of the test period, and to close the inlet valve after the expiry of said given period of time for which the outlet valve is closed.

2. Apparatus as set forth in claim 1 wherein the container includes level detecting means having a level switch operable to produce an electrical signal when the level of measuring liquid in the container reaches the switch, thereby to control operation of the time control means.

3. Apparatus as set forth in claim 2 wherein said level detecting means is vertically adjustable in the container.

4. Apparatus as set forth in claim 1 wherein said container further includes a filling pipe which extends into the vicinity of the outlet of the container, for introducing the measuring liquid which passes through the measuring filter into the container.

5. Apparatus as set forth in claim 1 wherein the pressure chamber of said pressure means is greater in height than the diameter of any air bubbles likely to occur in the liquid in the pressure chamber.

6. Apparatus as set forth in claim 1 wherein the container is of a stepped configuration comprising a plurality of portions of different diameters.

7. Apparatus as set forth in claim 1 wherein a screen means is disposed in the top portion of said container and supports the measuring filter, the screen means communicating with a funnel-like opening into the container and a filling pipe which extends into the vicinity of the container outlet being in flow communication with said opening for carrying liquid into the container from said filter.

8. Apparatus as set forth in claim 1 wherein said measuring filter is in the form of a movable filter strip which is passed stepwise from a supply reel to a take-up reel through the pressure chamber.

9. Apparatus for determining the colloid index of a liquid, comprising: conduit means for supplying measuring liquid from a body of liquid for the purposes of performing a colloid measuring operation on said measuring liquid; a measuring filter for filtering the measuring liquid supplied by the conduit means; below the measuring filter, a collecting and measuring container for collecting liquid which is passed through the filter; above the measuring filter, a pressure means including a pressure chamber for pressing measuring liquid through the filter; an inlet valve on said conduit means for controlling the flow of measuring liquid into the pressure chamber; an outlet valve at the outlet of the container, for controlling the discharge of measuring liquid therefrom; means for measuring the volume of liquid in the container; and a timing means for measuring periods of time for supplying liquid to and discharging liquid from the container, the arrangement being adapted to correlate volumes of liquid which are passed through the measuring filter and periods of time for which liquid is introduced into the container through the filter and accordingly to determine the change in the amount of liquid which flows through the filter with respect to time and use said change as a measurement in determining the colloid index.

* * * * *